(12) United States Patent
Cueni et al.

(10) Patent No.: US 7,434,483 B2
(45) Date of Patent: Oct. 14, 2008

(54) SAMPLE PIPETTE

(75) Inventors: Hansjörg Cueni, Stansstad (CH); Heiner Scherrer, Büsserach (CH)

(73) Assignee: CTC Analytics AG, Zwingen (CH)

( * ) Notice: Subject to any disclaimer, the term of this patent is extended or adjusted under 35 U.S.C. 154(b) by 28 days.

(21) Appl. No.: 10/575,721

(22) PCT Filed: Oct. 29, 2004

(86) PCT No.: PCT/CH2004/000654

§ 371 (c)(1),
(2), (4) Date: Apr. 25, 2006

(87) PCT Pub. No.: WO2005/042166

PCT Pub. Date: May 12, 2005

(65) Prior Publication Data

US 2007/0056350 A1    Mar. 15, 2007

(30) Foreign Application Priority Data

Oct. 31, 2003    (CH) .................................... 1858/03

(51) Int. Cl.
*B01L 3/02*    (2006.01)
(52) U.S. Cl. ............... 73/864; 73/864.01; 73/864.03; 422/100; 604/190

(58) Field of Classification Search ............... 73/864, 73/864.01, 864.03; 604/190
See application file for complete search history.

(56) References Cited

U.S. PATENT DOCUMENTS

| 4,001,929 | A | 1/1977 | Ishikawa |
| 4,316,462 | A | 2/1982 | Baker ..................... 604/190 |
| 4,435,176 | A | 3/1984 | Ishikawa |
| 4,737,150 | A * | 4/1988 | Baeumle et al. ............ 604/198 |
| 2003/0087454 | A1 | 5/2003 | Schultz et al. |

FOREIGN PATENT DOCUMENTS

| EP | 1 382 963 | 1/2004 |
| WO | WO 02/086488 | 10/2002 |

* cited by examiner

*Primary Examiner*—Daniel S Larkin
(74) *Attorney, Agent, or Firm*—Ladas & Parry LLP

(57) ABSTRACT

Sample pipettes used in particular for injecting samples into high pressure liquid chromatography apparatuses, which are provided with a hollow needle for drawing a sample and expelling same into a container or into a sample receiving device of the apparatus. An interchangeable cannula is mounted on the hollow needle of such a pipette, said cannula being capable of containing additional functional elements such as filters, chemically active phases and the like.

6 Claims, 1 Drawing Sheet

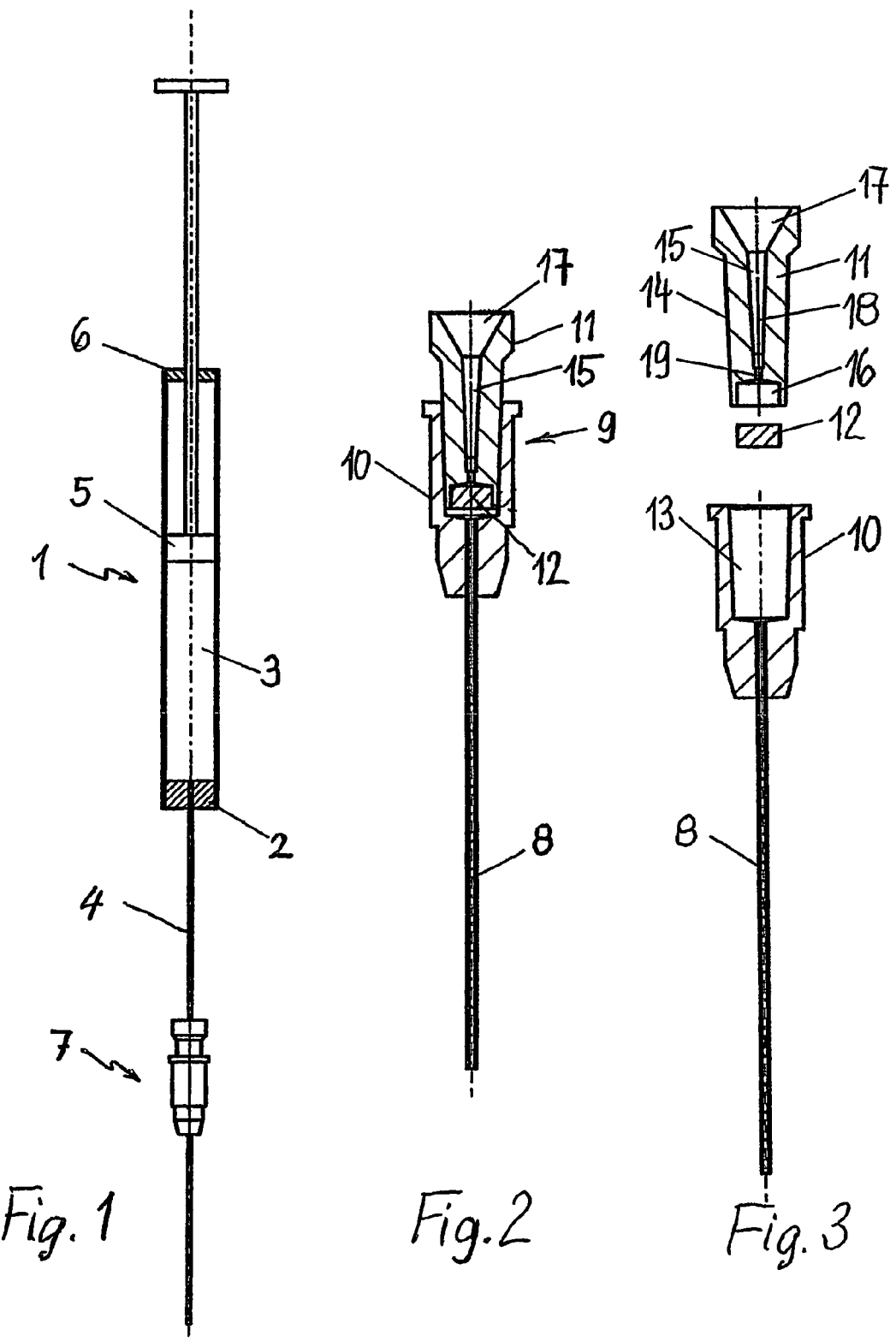

SAMPLE PIPETTE

FIELD OF THE INVENTION

The invention concerns a sample pipette having a hollow needle for drawing a liquid volume, such as a sample, a reagent, etc., and for expelling the same into a container or into a sample receiving device of an analysis apparatus, in particular for injecting the sample into a HPLC apparatus.

BACKGROUND OF THE INVENTION

Frequently, a sample preparation is required between a sample extraction and the input of the sample into a chromatography apparatus. For the associated necessary processing steps, such as filtering, separating or adding individual components, the sample has to be expelled from the extraction pipette into a processing container and, after the processing, drawn into a sample injector pipette.

A plurality of processing steps are costly and increase the risk of failures, contaminations, etc. Therefore, there exists basically a need for simplification also in the range of the sample preparation. The invention is based on this requirement.

SUMMURY OF THE INVENTION

According to the invention, a simplification is achieved by an interchangeable cannula consisting of an injection needle and an attachment part, mounted on the hollow needle, and being provided with functional elements, such as filters, coatings having active phases and the like.

As a rule, in the medical and related fields the term cannula is understood as describing an injection needle being adapted for injecting at one end and being provided with a sticking cone for connection with a syringe and the like at the other end. In the following descriptions, the term is used similarly, wherein there exists a special attachment part instead of the sticking cone. For distinguishing from the hollow needle of the syringe, the term injection needle is used for the one of the cannula.

BRIEF DESCRIPTION OF THE DRAWING FIGURES

The following embodiments of the invention will be described by referring to the appended drawings, wherein:

FIG. 1 shows a sample injector pipette having a mounted exchangeable cannula;

FIG. 2 shows a sectional illustration of the composed cannula; and

FIG. 3 shows a sectional elevational view of the single components of the cannula;

DETAILED DESCRIPTION OF THE DRAWING FIGURES

FIG. 1 shows the sample of the injector pipette in the shape of a syringe for manual sample injection into a HPLC apparatus. Essentially, the pipette consists of a cylinder 1, at one end 2 of which a hollow needle 4 connected to the inner space 3 thereof is arranged, and of a plunger 5 being movable axially in the inner space, which is operated from the other end 6 of the cylinder. Pipettes not being operated manually, but being a part of a system being operated by a machine, differ basically only negligibly therefrom. Therefore, the invention described in the following may be readily applied to a system operated by a machine.

A cannula 7 is arranged on the free end of the hollow needle 4, which is only sticked thereon and, therefore, can be easily exchanged. The cannula 7 is constructed for one single use, i.e. as a rule, a new cannula is used for each new sample. For certain working steps, it may be useful to exchange the cannula even between the drawing and the expelling of a sample, as it will be described below.

The cannula 7 shown in the sectional views in FIGS. 2 and 3 consists of an injection needle 8 and an attachment part 9. The attachment part 9 consists of a receiving sleeve 10, a sticking sleeve 11 being coaxially arranged therein and a functional element 12 arranged therebetween.

On one side, the receiving sleeve 10 is connected fixedly with the injection needle 8. From the other side thereof, a boring 13 being weakly conical extends to the injection needle 8. Essentially, the receiving sleeve 10 has the shape of the sticking cone of the Luer-type being known from commercially available cannulas. For the sake of simplicity, therefore, such commercially available cannulas can be used.

The sticking sleeve 11 has a conical outer wall 14 corresponding to the boring 13 and a continuous axial channel 15. At its end facing to the receiving sleeve, the channel 15 is expanded to a cylindrical chamber 16 which serves for receiving the functional element 12. A funnel-shaped extension 17 is formed at the other end of the channel 15, whereby the insertion of the hollow needle 4 is alleviated during exchanging the cannula. The centre part 18 of the channel 15 between the chamber 16 and the extension 17 is weakly conical or cylindrical and narrow so that it encloses tightly the hollow needle of the syringe. A narrow pass or bottleneck 19 is provided in front of the chamber for limiting the injection depth of the hollow needle.

The closed sides of the chamber 16 and the boring 13 are deepened conically. This results in flat cavities on both sides of the mounted functional element 12, which remain free.

For example, the functional element 12 comprises a filter. This serves for filtering a sample during drawing so as to separate components of the sample not being desired. In order to avoid contamination during the following injection of the thus filtered sample of the filtered components to be taken into an analysis apparatus, the cannula used for drawing is advisably removed or replaced by a new cannula with or without a filter.

An even distribution of the sample onto the complete active section is achieved by the flat cavities on both sides of the functional element 12.

It is also possible to draw a sample without a filter and, thereafter, to mount a cannula with a filter for filtering the sample during the sample injection.

The functional element 12 can be also a pack having an active phase, where components of the sample are adsorbed. These components can be solved again in a following step by a suitable solvent. As for filtering, these working steps are possible both during drawing and during expelling.

By a combination of the various steps and elements, a plurality of treatments of the samples may be realized. Therefore, a pipette provided with this cannula may be used for the sample preparation in a very advantageous manner. Samples which are treated by one or two various cannulas during drawing and expelling are delivered into a container, such as a cuvette of a micro titer plate, and, there, they are further processed by mixing and the like, before they are input into an analysis apparatus.

An essential advantage of the sample pipette according to the invention consists obviously in the fact that the liquid volume after the drawing into the hollow needle is present on the other side of the cannula. Thereby, it is possible to replace the cannula by another cannula before expelling.

Of course, the attachment part can also take shapes being different from the ones being shown in the present embodiment. For special steps during processing samples, there may be also provided cannulas, the attachment part of which comprises a larger inner volume. By use of such a cannula, a liquid volume can be only drawn into the cannula. For example, this can be useful if there exists already a sample within the hollow needle and a mixing shall be done during expelling.

The invention claimed is:

1. Sample pipette comprising a cylinder with a plunger being axially moveable inside the cylinder and being operated from a first end of the cylinder, a hollow needle for drawing a liquid volume into the cylinder and subsequently expelling it into a container or a sample receiving input of an analysis apparatus, the hollow needle being arranged at the second end of the cylinder, and an exchangeable cannula removeably fitted to a free end of the hollow needle, the cannula comprising an injection needle and, an attachment part fixedly connected to one end of the injection needle, the attachment part comprising a channel for receiving and tightly enclosing the tip of the hollow needle and housing a functional element.

2. Sample pipette according to claim 1, wherein the functional element comprises a filter.

3. Sample pipette according to claim 1, wherein the functional element comprises a chemically active phase.

4. Cannula for being attached to the tip of a hollow needle on a sample pipette comprising an injection needle and an attachment part fixedly connected to one end of the injection needle, the attachment part comprising a channel for receiving and tightly enclosing a tip of the hollow needle and housing a functional element.

5. Cannula according to claim 4, wherein the functional element comprises a filter.

6. Cannula according to claim 4, wherein the functional element comprises a chemically active phase.

* * * * *